(12) United States Patent
Guttag et al.

(10) Patent No.: US 11,568,982 B1
(45) Date of Patent: Jan. 31, 2023

(54) SYSTEM TO IMPROVE THE LOGISTICS OF CLINICAL CARE BY SELECTIVELY MATCHING PATIENTS TO PROVIDERS

(71) Applicant: Health at Scale Corporation, San Jose, CA (US)

(72) Inventors: John V. Guttag, Lexington, MA (US); Zeeshan H. Syed, Cupertino, CA (US)

(73) Assignee: HEALTH AT SCALE CORPORATION, San Jose, CA (US)

( * ) Notice: Subject to any disclaimer, the term of this patent is extended or adjusted under 35 U.S.C. 154(b) by 277 days.

(21) Appl. No.: 14/622,112

(22) Filed: Feb. 13, 2015

Related U.S. Application Data (60) Provisional application No. 61/940,574, filed on Feb. 17, 2014.

(51) Int. Cl.
  *G16H 40/20* (2018.01)
  *G16H 10/60* (2018.01)
(52) U.S. Cl.
  CPC ............. *G16H 40/20* (2018.01); *G16H 10/60* (2018.01)
(58) Field of Classification Search
  None
  See application file for complete search history.

(56) References Cited

U.S. PATENT DOCUMENTS

| | | |
|---|---|---|
| 7,191,150 B1 | 3/2007 | Shao |
| 7,853,456 B2 | 12/2010 | Soto et al. |

(Continued)

FOREIGN PATENT DOCUMENTS

| | | | |
|---|---|---|---|
| CA | 2715825 A1 * | 8/2009 | ............... A61B 5/00 |
| JP | 2017174406 A | 9/2017 | |

(Continued)

OTHER PUBLICATIONS

Bretthauer, K. M., & Cote, M. J. (1998). A model for planning resource requirements in health care organizations. Decision Sciences, 29(1), 243-270. Retrieved from https://search.proquest.com/docview/198106120?accountid=14753 (Year: 1998).*

(Continued)

*Primary Examiner* — Lena Najarian
(74) *Attorney, Agent, or Firm* — Morrison & Foerster LLP (57) ABSTRACT

A computer-based system and method to assign patients to providers. In one embodiment, the invention predicts the performance of provider-patient pairs in terms of different outcome-, financial- and satisfaction-related metrics across providers using advanced machine learning methodologies to develop distinct models for each of these metrics across each of the providers using a historical database. In another embodiment, patients are assigned to providers in a batch or online manner using this information through an optimization framework that looks to maximize or minimize arbitrary combinations of the outcome-, financial-, and satisfaction-related metrics subject to practical operational constraints. In another embodiment, the invention includes logic to avoid 'boxing' providers and uses exploration to continuously update the profiles of providers for metrics in a manner that accounts for provider performance getting better or worse over time, and the historical database not being representative of all potential patients to be assigned by this system.

20 Claims, 2 Drawing Sheets

(56) References Cited

U.S. PATENT DOCUMENTS

| | | |
|---|---|---|
| 8,417,541 B1 | 4/2013 | Kramer |
| 8,548,937 B2 | 10/2013 | Saigal et al. |
| 10,943,676 B2 | 3/2021 | Farooq et al. |
| 11,114,204 B1 | 9/2021 | Guttag et al. |
| 2003/0135128 A1 | 7/2003 | Suffin |
| 2004/0107088 A1 | 6/2004 | Budzinski |
| 2006/0173663 A1 | 8/2006 | Langheier |
| 2006/0206359 A1 | 9/2006 | Stang |
| 2007/0088577 A1 | 4/2007 | Carter et al. |
| 2007/0269804 A1 | 11/2007 | Liew |
| 2009/0093689 A1 | 4/2009 | Schuppert et al. |
| 2009/0259550 A1* | 10/2009 | Mihelich ............... G06Q 30/02 705/14.42 |
| 2010/0184093 A1 | 7/2010 | Donovan |
| 2011/0082712 A1 | 4/2011 | Eberhardt, III |
| 2011/0295621 A1 | 12/2011 | Farooq et al. |
| 2012/0041330 A1 | 2/2012 | Prichep et al. |
| 2012/0066217 A1 | 3/2012 | Eder |
| 2012/0095943 A1* | 4/2012 | Yankov ................ G06N 99/005 706/12 |
| 2012/0109683 A1* | 5/2012 | Ebadollahi ............ G06Q 50/24 705/3 |
| 2012/0179002 A1 | 7/2012 | Brunetti et al. |
| 2013/0022953 A1* | 1/2013 | van der Linden ....... G09B 7/02 434/322 |
| 2013/0096948 A1 | 4/2013 | Parkinson |
| 2013/0185096 A1 | 7/2013 | Giusti |
| 2013/0197925 A1 | 8/2013 | Blue |
| 2013/0225439 A1 | 8/2013 | Princen et al. |
| 2014/0058755 A1 | 2/2014 | Macoviak |
| 2014/0108034 A1* | 4/2014 | Akbay .............. G06Q 10/06315 705/2 |
| 2014/0200824 A1 | 7/2014 | Pancoska |
| 2014/0371610 A1 | 12/2014 | Liu et al. |
| 2015/0006456 A1 | 1/2015 | Sudharsan |
| 2015/0046181 A1 | 2/2015 | Adjaoute |
| 2015/0073943 A1 | 3/2015 | Norris et al. |
| 2015/0100336 A1 | 4/2015 | Ford et al. |
| 2015/0100349 A1 | 4/2015 | Lacy et al. |
| 2015/0161331 A1 | 6/2015 | Oleynik |
| 2015/0164453 A1 | 6/2015 | Choi et al. |
| 2015/0248534 A1 | 9/2015 | Krzywicki et al. |
| 2015/0278470 A1 | 10/2015 | Bakker |
| 2015/0289795 A1 | 10/2015 | Batlle Gómez |
| 2015/0294075 A1 | 10/2015 | Rinaldo |
| 2015/0317449 A1 | 11/2015 | Eder |
| 2015/0367145 A1 | 12/2015 | Sjölund et al. |
| 2016/0012202 A1 | 1/2016 | Hu et al. |
| 2016/0135706 A1 | 5/2016 | Sullivan et al. |
| 2016/0147959 A1 | 5/2016 | Mariottini et al. |
| 2016/0196398 A1 | 7/2016 | Vivero et al. |
| 2016/0203217 A1 | 7/2016 | Anisingaraju et al. |
| 2016/0259883 A1 | 9/2016 | Grinchuk et al. |
| 2016/0378943 A1 | 12/2016 | Vallée |
| 2017/0073761 A1 | 3/2017 | Harkin et al. |
| 2017/0083682 A1 | 3/2017 | Mcnutt |
| 2017/0101093 A1 | 4/2017 | Barfield, Jr. et al. |
| 2017/0124269 A1 | 5/2017 | Mcnair |
| 2017/0185723 A1 | 6/2017 | Mccallum et al. |
| 2017/0277856 A1 | 9/2017 | De La Torre et al. |
| 2017/0308671 A1 | 10/2017 | Bahrami et al. |
| 2017/0316180 A1 | 11/2017 | Takeda et al. |
| 2018/0121619 A1 | 5/2018 | Perlroth et al. |
| 2018/0214105 A1 | 8/2018 | Anavi et al. |
| 2019/0043606 A1 | 2/2019 | Roots et al. |
| 2019/0172587 A1 | 6/2019 | Park et al. |
| 2019/0333613 A1 | 10/2019 | Zaidi et al. |
| 2019/0371450 A1 | 12/2019 | Lou et al. |
| 2020/0074313 A1 | 3/2020 | Sharifi Sedeh et al. |
| 2021/0035693 A1 | 2/2021 | Mohammad et al. |
| 2021/0065909 A1 | 3/2021 | Donaldson |
| 2021/0090748 A1 | 3/2021 | Toyoshlba et al. |
| 2021/0118559 A1 | 4/2021 | Lefkofsky |
| 2021/0221404 A1 | 7/2021 | Reiner et al. |
| 2021/0249138 A1 | 8/2021 | Hayashitani et al. |

FOREIGN PATENT DOCUMENTS

| | | |
|---|---|---|
| WO | 2015157576 A1 | 10/2015 |
| WO | 2016120955 A1 | 8/2016 |
| WO | 2019212005 | 11/2019 |
| WO | 2020081609 A1 | 4/2020 |

OTHER PUBLICATIONS

Tan, Kar Way. "Dynamic Queue Management for Hospital Emergency Room Services." Order No. 10169843 Singapore Management University (Singapore), 2013. Ann Arbor: ProQuest. Web. Aug. 25, 2022. (Year: 2013).*

Non-Final Office Action dated Sep. 22, 2017, for U.S. Appl. No. 14/678,349, filed Apr. 3, 2015, thirteen pages. (2.00).

Final Office Action dated Dec. 26, 2018, for U.S. Appl. No. 14/809,528, filed Jul. 27, 2015, 30 pages.

Final Office Action dated Jan. 7, 2019, for U.S. Appl. No. 14/736,470, filed Jun. 11, 2015, fifteen pages.

Final Office Action dated May 3, 2018, for U.S. Appl. No. 14/678,349, filed Apr. 3, 2015, twenty one pages.

Non-Final Office Action dated Dec. 18, 2019, for U.S. Appl. No. 14/678,349, filed Apr. 3, 2015, eleven pages.

Non-Final Office Action dated Feb. 26, 2018, for U.S. Appl. No. 14/736,470, filed Jun. 11, 2015, sixteen pages.

Non-Final Office Action dated Jan. 10, 2019, for U.S. Appl. No. 14/678,349, filed Apr. 3, 2015, twenty two pages.

Non-Final Office Action dated Jan. 29, 2020, for U.S. Appl. No. 14/809,528, filed Jul. 27, 2015, 20 pages.

Non-Final Office Action dated Mar. 9, 2020, for U.S. Appl. No. 14/736,470, filed Jun. 11, 2015, nine pages.

Non-Final Office Action dated May 1, 2018, for U.S. Appl. No. 14/809,528, filed Jul. 27, 2015, 25 pages.

Final Office Action dated Jul. 21, 2020, for U.S. Appl. No. 14/809,528, filed Jul. 27, 2015, twenty pages.

Final Office Action dated Jul. 21, 2020, for U.S. Appl. No. 14/678,349, filed Apr. 3, 2015, twelve pages.

Final Office Action dated Nov. 16, 2020, for U.S. Appl. No. 14/736,470, filed Jun. 11, 2015, eleven pages.

Notice of Allowance dated Jul. 28, 2021, for U.S. Appl. No. 14/678,349, filed Apr. 3, 2015, eleven pages.

Caruana, Rich. (1997). "Multitask Learning," Kluwer Academic Publishers, Manufactured in the Netherlands, Machine Learning, 35 pages.

Caruana, Rich. (May 1996). "Algorithms and Applications for Multitask Learning," School of Computer Science, Carnegie Mellon University, Pittsburgh, PA, 9 pages.

Non-Final Office Action dated Jan. 29, 2021, for U.S. Appl. No. 14/678,349, filed Apr. 3, 2015, eight pages.

Baechle, C., et al., "Latent topic ensemble learning for hospital readmission cost optimization," European Journal of Operational Research 281 (2020) 517-531. (Year: 2019).

Brakenhoff, T. B., et al. (2018). "Investigating Risk Adjustment Methods for Health Care Provider Profiling When Observations are Scarce or Events Rare". Health Services Insights, vol. 11, 1-10, doi: http://dx.doi.org/10.1177/1178632918785133, (Year:2018).

Final Office Action dated Jul. 12, 2022, for U.S. Appl. No. 16/853,621, filed Apr. 20, 2020, twenty three pages.

Li, Xiull et al., "Lung Nodule Malignancy Prediction Using Multitask Convolutional Neural Network," Proc. of SPIE vol. 10134, 1013424-1 (Year: 2017).

Non-Final Office Action dated Aug. 27, 2021, for U.S. Appl. No. 14/809,528, filed Jul. 27, 2015, 14 pages.

Non-Final Office Action dated Feb. 8, 2022, for U.S. Appl. No. 16/853,621, filed Apr. 20, 2020, 27 pages.

Non-Final Office Action dated Jul. 27, 2022, for U.S. Appl. No. 16/875,835, filed May 15, 2020, 48 pages.

(56) References Cited

OTHER PUBLICATIONS

Non-Final Office Action dated Mar. 18, 2022, for U.S. Appl. No. 14/736,470, filed Jun. 11, 2015, 14 pages.

Rahimian, F., et al., "Predicting the risk of emergency admission with machine learning: Development and validation using linked electronic health records," PLOS Medicine, Nov. 20, 2018, pp. 1-18 (Year: 2018).

Ruder, Sebastian. "An Overview of Multi-Task Learning in Deep Neural Networks," https://ruder.io/muiti-task/ (Year: 2017).

Final Office Action dated Oct. 4, 2022, for U.S. Appl. No. 14/736,470, filed Jun. 11, 2015, thirteen pages.

* cited by examiner

SYSTEM TO IMPROVE THE LOGISTICS OF CLINICAL CARE BY SELECTIVELY MATCHING PATIENTS TO PROVIDERS

RELATED APPLICATIONS

This application claims priority to U.S. Provisional Application 61/940,574 filed Feb. 17, 2014, the entirety of which is herein incorporated by reference.

FIELD OF THE INVENTION

The present invention relates generally to a computer system to selectively match patients to healthcare providers (e.g., hospitals, clinics, physicians, nurses) in a manner that simultaneously considers improvements in outcomes, satisfaction, and finances as well as the need to meet different operational constraints.

BACKGROUND OF THE INVENTION

Within a single geographic market, medical providers differ in quality, cost, and price of service. Existing approaches to match patients to healthcare providers are ad hoc and subjective. In many cases, patients will continue to visit the same providers that have treated them previously when making determinations for new episodes of care—despite variations in both patient health and needs, as well as in provider abilities on different tasks. In other cases, patients will seek new providers based entirely on third-party rankings, reviews from other patients, or recommendations from existing caregivers. In these cases, this approach is highly subjective and non-empirical. As a result of this, the existing delivery of care is sub-optimal. Patients experience worse outcomes (as well as lower satisfaction and higher co-pays) than if they were intelligently matched to providers suited for their individual conditions. Similarly, providers and payers are adversely affected in terms of reputation and finances due to an inability to match the specific needs of patients to the capabilities of the providers for each new episode of care.

Recent art has focused on using a computer model to predict which physicians might result in desirable outcomes for a patient. This approach reduces patients to features (e.g., age, gender, weight) and physicians to features (e.g., years of training, sub-specialty). It then trains a model on historical data from multiple patients and physician encounters to determine how different features of the patients and physician jointly correspond to outcomes. This information can be used to make predictions about new patient and physician combinations by passing features of these patients and physicians through the model. While a step in the right direction, this approach is limited in different ways.

For example, reducing physicians to a coarse set of features loses significant information about providers and fails to account for variations between two or more physicians who might, for example, have similar training and sub-specialty but may still differ in outcomes based on characteristics not accounted for in the feature set. While using a richer feature set is an option to try and mitigate this effect, it is associated with other issues (such as model over-fitting). What would be preferable in this case is an approach that does not have to abstract providers into a set of features but can distinctly preserve the identity of these providers during the course of modeling. As another example of the limitation in modeling methodology, any attempt to develop a single computational model by pooling data from across multiple physician and patient encounters is also limited in that it is easily biased by physicians with far more available training data than others. Due to the contribution of substantially more data by these physicians for model construction, information about providers with fewer cases is washed out. In this setting again, it would be preferable to avoid merging data from different providers by reducing it to coarse feature sets and to retain the distinct identity and information about the providers for modeling.

A second set of issues associated with the existing art of using a computer model to predict which providers might result in desirable outcomes for a patient is that this approach does not provide any intelligence in how to assign patients to providers. Many providers, for example, can only accommodate a limited number of patients. In this setting, it not sufficient to simply determine which providers will be the best one for a patient. Instead, there is a need for more intelligent allocation that can account for operational constraints and exploit opportunities for improvements in not just outcomes but also satisfaction, finances and other such metrics adhering to practical or policy restrictions across providers.

A third set of issues is related to a focus on only a single quantity of interest: patient outcomes. In many practical scenarios, there are multiple quantities that are of interest, e.g., outcomes, cost, margin, revenue, satisfaction etc. In such a setting, an approach that can more intelligently address the multiple needs of clinical care from the perspective of patients, providers, and payers would be desirable.

A fourth set of issues associated with the existing art is that it risks "boxing" providers into certain categories based on their previous performance. For example, if a provider does poorly initially on a set of patients then the existing art would not recommend that any other patients see that provider despite the provider potentially taking steps that will allow improvement for these cases. In this case, it is preferable for an allocation approach that performs exploration and has memory that decays over time to gracefully address the possibility of improvement or worsening of performance.

SUMMARY OF THE INVENTION

In one aspect, the present invention relates to a computer system that can selectively match patients to healthcare providers. In one embodiment, provider is defined broadly to include hospital, clinics, doctors, nurses, teams, etc., as well as combinations (e.g., physician and location) so that the present invention allows for patient assignments to be made that determine both who should treat the patient as well as where the patient should be treated. The system can be used both by patients and providers.

The invention proposes novel machine learning to simultaneously construct multiple models that can accurately predict the outcomes, finances, and satisfaction separately for each provider individually. The ability to produce multiple models—one for each provider for each metric—using this novel machine learning-based approach avoids the need to both reduce providers to features that lose information and to lump data together from multiple providers in a single model affected by issues of prevalence and heterogeneity. Instead, the invention exploits shared structure between the tasks of predicting outcomes, finances, and satisfaction across providers to construct individualized models for each provider even in the presence of small sample sizes for training.

The invention further uses information about how the outcomes, finances, and satisfaction vary for patients across providers to allocate patients to providers in a manner designed to achieve high levels of performance for these metrics. Specifically, the invention proposes optimization methodology that can be used in batch or online mode to assign patients to providers in a manner that meets any specified constraints (e.g., the maximum/minimum number of patients a provider can treat; the maximum/minimum outcome, satisfaction, and financial targets associated with providers; and other constraints associated with operational considerations). In this manner, the invention makes information about varying patient outcomes, finances, and satisfaction across providers actionable in the face of practical resource considerations and constraints. It provides a means to assign cases in a manner that ensures there is no additional burden on providers, but the patient mix being seen is intelligently re-adjusted to significantly improve care.

The invention finally also comprises an exploratory and memory-based component that weights more recent data more heavily while making determinations of patient assignments across providers—allowing for recent changes and trends in provider performance to be given more importance relative to potentially outdated historical data. The exploratory component also allows for intelligent assignment of cases with uncertainty to providers to maximally learn how they would perform on unseen patients; thereby allowing for providers to avoid being "boxed" into specific types.

While the invention is proposed here in terms of exploiting opportunities to improve the logistics of clinical care, it may have added value in other domains, e.g., online education in which learners can similarly be matched to optimal educators.

BRIEF DESCRIPTION OF THE DRAWINGS

The structure and function of the invention can be best understood from the description herein in conjunction with the accompanying figures. The figures are not necessarily to scale, emphasis instead generally being placed upon illustrative principles. The figures are to be considered illustrative in all aspects and are not intended to limit the invention, the scope of which is defined only by the claims.

DETAILED DESCRIPTION OF EMBODIMENTS

Figure 1:
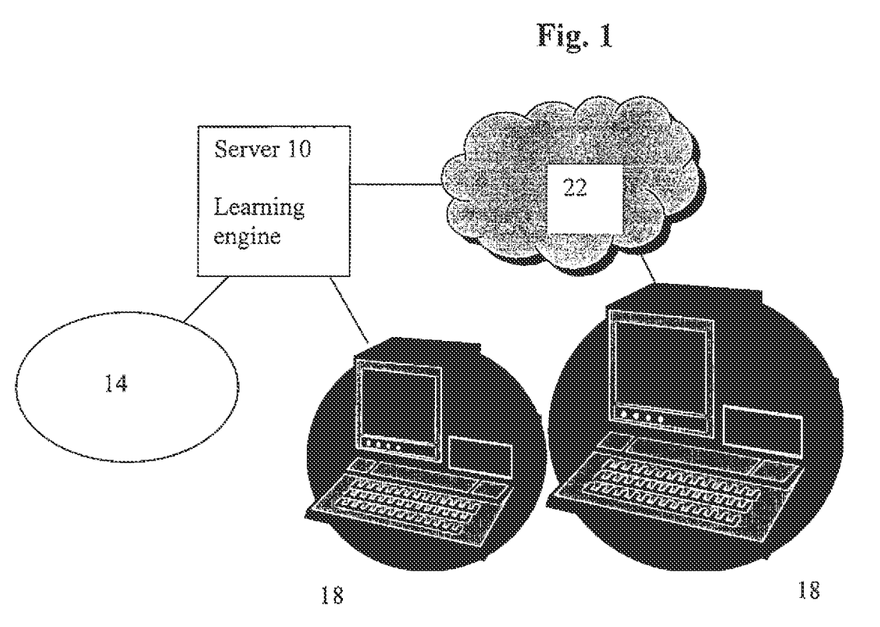
FIG. 1 is a block diagram of an embodiment of the system constructed in accordance with the invention.

Referring to FIG. 1 and in brief overview, a system constructed in accordance with the invention includes a server (10) in communication with a database (14) and one or more input/output devices (generally 18) which may be in communication with the server over a network (22). The server 10 includes a learning machine executing multiple models.

Figure 2:
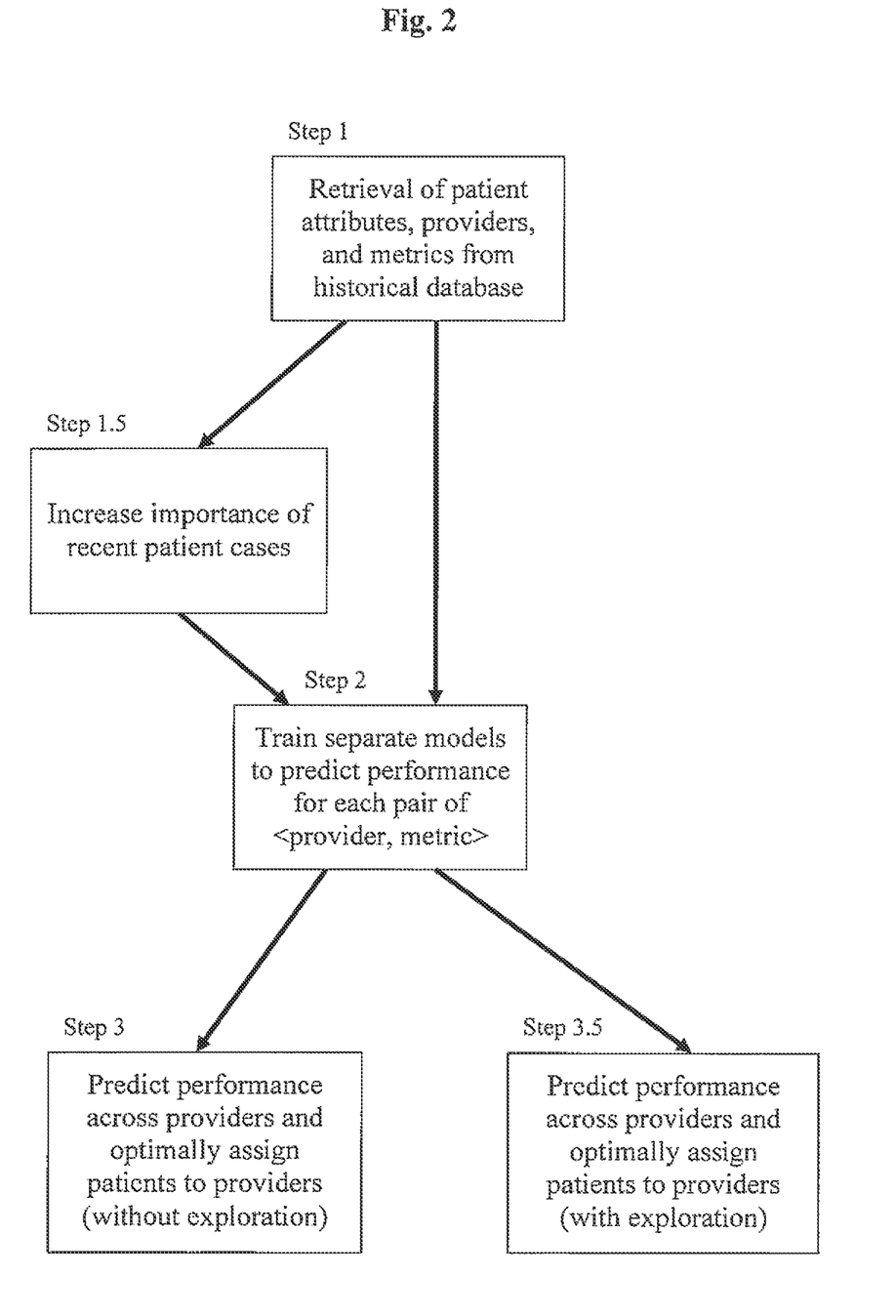
FIG. 2 illustrates a flow diagram of the system to allocate patients to providers in a manner designed to improve different metrics subject to operational constraints.

Referring to FIG. 2, this FIG. illustrates an embodiment of a flow diagram constructed in accordance with the invention. The steps shown are described below in more detail.

Step 1: Initially, historical patient case records are located in the database (14). In this database 14, each patient previously treated by any provider is associated with a plurality of attributes based on but not limited to the patient's demographics (e.g., age, gender); history (e.g., prior myocardial infarction) and physical exam findings (e.g., edema around the ankles); comorbidities (e.g., hypertension); laboratory reports (e.g., high troponin levels; low ejection fraction); admission type (e.g., transfer from another hospital, elective admission); and insurance (e.g., Medicare). This plurality of attributes is designated as a vector and this vector is denoted as $x_i$. Such a vector of patient attributes that is associated with each patient is designated as $x_i$ where i=1 . . . N for a total of N patients in the database and $x_i(j)$ is the value of the j-th attribute for patient i out of a total of d possible attributes. Each patient is also associated with a scalar indicator $p_i$ that indicates the provider who treated patient i in the database and where $p_i \in \{1, \ldots, M\}$ for a total of M providers in the database. For cases where patients are seen by more than one provider, they can be represented as multiple entries in the database to retain this information about multiple providers. Each patient is also associated with a vector $y_i$ comprising the metrics of interest to be modeled (e.g., outcome, cost, margin, revenue, satisfaction, length of stay etc.) as they were historically observed for the patient in the database. Consistent with the notation used for patient attributes above, $y_i(j)$ corresponds to the j-th metric of interest for patient i.

Step 2: For every metric, the system simultaneously learns multiple models—one for each provider—that predict the value of the metric given the patient data for that provider. In this manner, the system simultaneously learns separate models for each metric across all providers that can be used to predict how new patients would respond when treated by these providers. In one embodiment, this simultaneous learning of multiple models is done through the machine learning approach of multi-task learning. This approach uses the following notation presented more formally below: the vector $W_i$ for i=1, . . . , M represents the weight vector for the model predicting the metric of interest for provider i; the matrix W comprises the matrix produced by stacking together the vectors $W_i$; the matrix $X_i$ corresponds to a matrix with the patient attribute vectors stacked together for all patients treated by the provider $i_i$; $X_{i,j}$ represents the j-th patient attribute vector in the matrix $X_i$; $Y_i$ corresponds to the value of the metric of interest for these patients treated by provider i; $Y_{i,j}$ represents the metric for the j-th patient in the vector $Y_i$; $\|.\|_1$ is the L1 norm; $\|.\|_F$ is the L2 Frobenius norm; $\|.\|_{2,1}$ is the L2,1 norm; $\|.\|_{1,\infty}$ is the L1,∞ norm; $\|.\|^*$ is the trace norm; $r_1$ is the regularization parameter controlling the L1 norm; and $r_F$ is the regularization parameter controlling the L2 Frobenius norm. There are different ways to formulate the goal for simultaneously learning multiple models across providers for each metric using multi-task learning. These include the following:

(1) multi-task Lasso with least squares loss:

$$\min_W \sum_{i=1}^{M} \|W_i^T X_i - Y_i\|_F^2 + r_1 \|W\|_1 + r_F \|W\|_F^2$$

which can alternatively be expressed with a logistic loss (using $n_i$ to denote the patients treated by provider i) as:

$$\min_W \sum_{i=1}^{M} \sum_{j=1}^{n_i} \log\left(1 + \exp\left(-Y_{i,j}\left(W_i^T X_{i,j}\right)\right)\right) + r_1 \|W\|_1 + r_F \|W\|_F^2$$

(2) multi-task $L_{2,1}$-norm regularization with least squares loss (which may be expressed with a logistic loss similar to (1) above—logistic loss formulation here omitted for brevity):

$$\min_{W} \sum_{i=1}^{M} \|W_i^T X_i - Y_i\|_F^2 + r_1 \|W\|_{2,1} + r_F \|W\|_F^2$$

(3) dirty multi-task learning with least squares loss (which may be expressed with a logistic loss similar to (1) above—omitted for brevity):

$$\min_{W} \sum_{i=1}^{M} \|W_i^T X_i - Y_i\|_F^2 + r_1 \|P\|_{1,\infty} + r_F \|Q\|_1$$

$$\text{s.t. } W = P + Q$$

where P is the group sparsity component and Q is the elementwise sparse component of the matrix W.

(4) sparse graph regularized multi-task learning with least squares loss (which may be expressed with a logistic loss similar to (1) above—omitted for brevity):

$$\min_{W} \sum_{i=1}^{M} \|W_i^T X_i - Y_i\|_F^2 + r_1 \|WR\|_F^2 + r_F \|W\|_F^2 + r_F \|W\|_1$$

where additionally R is used to represent a graph between providers in a matrix form where knowledge about how providers might be similar can be leveraged through edges between them.

(5) multi-task learning using trace-norm regularization with least squares loss (which may be expressed with a logistic loss similar to (1) above—omitted for brevity):

$$\min_{W} \sum_{i=1}^{M} \|W_i^T X_i - Y_i\|_F^2 + r_1 \|W\|_*$$

(6) multi-task learning with incoherent sparse and low-rank components using least squares loss (which may be expressed with a logistic loss similar to (1) above—omitted for brevity):

$$\min_{W} \sum_{i=1}^{M} \|W_i^T X_i - Y_i\|_F^2 + r_1 \|P\|_1$$

$$\text{s.t. } W = P + Q$$

$$\|Q\|_* \leq r_F$$

(7) multi-task learning with convex related clusters and least squares loss (which may be expressed with a logistic loss similar to (1) above—omitted for brevity):

$$\min_{W,H} \sum_{i=1}^{M} \|W_i^T X_i - Y_i\|_F^2 + r_1 \eta (1+\eta) tr(W(\eta I + H)^{-1} W^T)$$

$$\text{s.t. } tr(H) = k$$

$$H \rho I$$

$$H \in S_+^M$$

$$\eta = \frac{r_F}{r_1}$$

where additionally the providers are believed to be organized into k clusters. Introducing the additional notation here: η corresponds to the ratio between the regularization parameters controlling the L2 Frobenius norm and the L1 norm; and H is an intermediate matrix that is symmetric positive semi-definite (specifically, $S_+^M$ represents a matrix that is symmetric positive semi-definite and is of size M by M, tr(.) represents the trace operation, and HρI denotes that I–H is positive semi-definite).

(8) multi-task learning with convex relaxed alternating structure optimization with least squares loss (which may be expressed with a logistic loss similar to (1) above—omitted for brevity):

$$\min_{W} \sum_{i=1}^{M} \|W_i^T X_i - Y_i\|_F^2 + r_1 \eta (1+\eta) tr(W^T (\eta I + H)^{-1} W)$$

$$\text{s.t. } tr(H) = k$$

$$H \prec I$$

$$H \in S_+^d$$

$$\eta = \frac{r_F}{r_1}$$

where the notation is similar to (8) above except, $S_+^M$ here represents a matrix that is symmetric positive semi-definite and is of size d by d.

(9) robust multi-task learning with least squares loss (which may be expressed with a logistic loss similar to (1) above—omitted for brevity):

$$\min_{W} \sum_{i=1}^{M} \|W_i^T X_i - Y_i\|_F^2 + r_1 \|L\|_* + r_F \|K\|_{1,2}$$

$$\text{s.t. } W = L + K$$

where L is a low rank structure matrix reflecting task relatedness and K is a group-sparse structure matrix to detect outliers.

(10) convex sparse fused group multi-task learning with least squares loss (which may be expressed with a logistic loss similar to (1) above—omitted for brevity):

$$\min_{W} \sum_{i=1}^{M} \|W_i^T X_i - Y_i\|_F^2 + r_F \|RW^T\|_1 + r_3 \|W\|_{2,1} + r_1 \|W\|_1$$

where $r_3$ controls group sparsity for joint feature selection and R represents the structure variable.

(11) non-convex sparse fused group multi-task learning with least squares loss (which may be expressed with a logistic loss similar to (1) above—omitted for brevity):

$$\min_W \sum_{i=1}^M \|W_i^T X_i - Y_i\|_F^2 + r_F \|RW^T\|_1 + r_1 \sum_{i=1}^d \sqrt{\|w_i\|_1}$$

where R represents the structure variable and $w_i$ is the vector corresponding to the coefficients of the models for the i-th patient attribute across all providers.

(12) incomplete multi-source fusion multi-task learning with least squares loss (which may be expressed with a logistic loss similar to (1) above—omitted for brevity):

$$\min_W \frac{1}{M} \sum_{i=1}^M \frac{1}{n_i} \|W_i^T X_i - Y_i\|_F^2 + r_1 \sum_{s=1}^S \sum_{k=1}^{d_s} \|W_{G(s,k)}\|_2$$

where the patient attributes can be divided into S groups of features (e.g., demographics, comorbidities, etc.); $d_l$ represents the number of patient attributes in group l; and $W_{G(s,k)}$ gives all the model parameters corresponding to the k-th patient attribute in the s-th feature group.

(13) multi-stage feature learning multi-task learning with least squares loss (which may be expressed with a logistic loss similar to (1) above—omitted for brevity):

$$\min_W \frac{1}{M} \sum_{i=1}^M \frac{1}{n_i} \|W_i^T X_i - Y_i\|_F^2 + r_1 \sum_{j=1}^d \min(\|w_j\|_1, \phi)$$

where $\phi$ is the cap for the L1 norm.

The choice of approach for multi-task learning can be made on the basis of cross-validation error. In other embodiments, the simultaneous learning of multiple models may also be performed by use of approaches other than multi-task learning (e.g., transfer learning, semi-supervised learning, unsupervised learning, metric or subspace learning, or 1.5 class learning).

The final product of Step 2 is to use information from the database in Step 1 to train for each metric separate models for every provider to predict how they would perform on patients with given attributes. In this way, Step 2 provides a way to simultaneously learn predictive models for each <provider, metric> pair that can be used to estimate performance on a new patient.

Step 3: An assignment is made of new patients using the predictive models for each <provider, metric> pair arising from Step 2 in a manner that looks to optimize different performance metrics while adhering to any specified operational constraints. In one embodiment, this is done in a batch manner, i.e., when a group of patients present to be assigned to providers simultaneously. Specifically, models for each <provider, metric> pair are used to predict how new patients can be expected to respond across different providers for different metrics. Representing the predicted value for patient i when treated by provider j for metric k as z(i,j,k) and using the indicator variables f(i,j) it is possible to to identify whether patient i should be assigned to provider j or not (0='false' and 1='true'). An assignment of a batch of patients for a particular metric is determined in Step 3 by solving either the following maximization problem (for metrics that are to be maximized, e.g., revenue) across providers:

$$\max_f \sum_{i=1}^N \sum_{j=1}^M z(i,j,k) f(i,j)$$

$$\text{s.t.} \sum_{j=1}^M f(i,j) = 1 \forall i = 1, \ldots, N$$

$$\sum_{i=1}^N f(i,j) \geq \varphi_{Lo,j} \forall j = 1, \ldots, M$$

$$\sum_{i=1}^N f(i,j) \leq \varphi_{Hi,j} \forall j = 1, \ldots, M$$

$$f(i,j) \in \{0, 1\}$$

or by solving the following minimization problem (for metrics that are to be minimized, e.g., clinical complications) across providers:

$$\min_f \sum_{i=1}^N \sum_{j=1}^M z(i,j,k) f(i,j)$$

$$\text{s.t.} \sum_{j=1}^M f(i,j) = 1 \forall i = 1, \ldots, N$$

$$\sum_{i=1}^N f(i,j) \geq \varphi_{Lo,j} \forall j = 1, \ldots, M$$

$$\sum_{i=1}^N f(i,j) \leq \varphi_{Hi,j} \forall j = 1, \ldots, M$$

$$f(i,j) \in \{0, 1\}$$

The optimization problems above maximize or minimize a particular metric such that each patient is assigned to a single provider, and the total number of patients seen by a provider is required to lie within a range (e.g., ensuring that no provider j sees fewer than $\varphi_{Lo,j}$ cases and no more than $\varphi_{Hi,j}$ cases). Note that the distinction between maximization and minimization is minor as the minimization problem can be converted to a maximization problem (and vice versa) by taking the negative of the objective function.

If there is more than one metric of interest, in another embodiment the optimization problems above are augmented to reflect these additional metrics in both the constraints (e.g., add additional constraints that maximize revenue while mandating that clinical complications be below a given threshold) and the objective function (e.g., minimize or maximize a weighted sum of metrics in the objective function). This can be represented as a more generalized optimization problem as follows (without loss of generality, the maximization case is shown here and note that minimization in the objective function and constraints can be re-expressed as maximization by taking the negative):

$$\max_f \sum_{i=1}^N \sum_{j=1}^M f(i,j) \left[ \sum_{k=1}^K z(i,j,k) u_k \right]$$

$$\text{s.t.} \sum_{j=1}^M f(i,j) = 1 \forall i = 1, \ldots, N$$

$$\sum_{i=1}^N f(i,j) \geq \varphi_{Lo,j} \forall j = 1, \ldots, M$$

-continued $$\sum_{i=1}^{N} f(i, j) \leq \varphi_{Hi,j} \forall\, j = 1, \ldots, M$$

$$\sum_{i=1}^{N}\sum_{j=1}^{M} f(i, j)z(i, j, k) \geq Met_{Lo,k} \forall\, k = 1, \ldots, K$$

$$\sum_{i=1}^{N}\sum_{j=1}^{M} f(i, j)z(i, j, k) \leq Met_{Hi,k} \forall\, k = 1, \ldots, K$$

$$f(i, j) \in \{0, 1\}$$

where additionally the $u_k$ represent positive or negative weights (that may reward or penalize) for the different metrics, and the thresholds $Met_{LO,k}$ and $Met_{HI,k}$ impose constraints on maximum and minimum values for the metrics. Note that the formulations above can be simply extended to support a large number of arbitrary operational constraints (e.g., fractional assignments across providers, constraints on metrics across all patients and providers or within groups of patients or providers, constraints comprising multiple-metrics, constraints on individual patients or providers, etc.). For brevity, not all such combinations of optimization problems are presented here.

In a further embodiment, the invention is used to assign patients presenting in an online manner (rather than the batch approach described above) to providers subject to operational constraints. This is done using statistical priors extracted from the historical data in Step 1 on the probabilistic characteristics with which patients present with different attributes. Using this information, when a new patient presents, the probabilistic priors are sampled multiple times to construct a synthetic set of patients that will present within a given time-frame of assignment, and the optimization problem is solved in a batch setting using this simulated data. This is repeated multiple times and the new patient is assigned to the provider determined to be optimal in aggregate on these simulated runs. In another embodiment, an online optimization approach is used to obtain an assignment that is within a pre-specified bounded error ("competitive ratio") of the assignment that would be possible if all patients had presented as a batch. In yet another embodiment, the notion of optimality is a local one, i.e., at each stage a locally optimal ("greedy") assignment of the patient is made subject to the constraints and objective functions.

Step 1.5: To address the issue of 'boxing' providers into specific types, decaying memory is introduced within the system. This is intended to prevent providers from being constrained into doing only specific sets of procedures based on a small number of good or bad results on an initial set of patients. To achieve this, the invention makes use of an optional step between Step 1 and Step 2 where patient data from Step 1 that is more recent is accorded increased importance during the simultaneous training of models for each <provider, metric> pair in Step 2. In one embodiment, this is done by oversampling recent data (with the rate of oversampling increasing along a continuous scale based on recency). In another embodiment, the importance of recent data is increased by assigning this data a higher weight during the multi-task learning formulations proposed in Step 2. Specifically, the least squares norm $\|W_i^T X_i - Y_i\|_F^2$ for each provider in the formulations for Step 2 is augmented with recency weights such that the error for any patient i is given by $(W_i^T x_i - y_i) q_i$ where $q_i$ corresponds to the recency weight for patient i.

Step 3.5: As a further means of avoiding a 'boxing' of providers into specific types, the invention also makes use of an augmented version of Step 3 (which can be used as a substitute to the approach detailed above). In this case, the optimization problem includes an additional component representing reward for exploring areas of uncertainty with regard to provider performance. In one embodiment, this reward is based on the active learning approach of querying points in the margin of the model for each provider. In another embodiment, this reward is based on a multi-armed bandit approach. Denoting the reward of assigning patient i to provider j as g(i,j), for example, the optimization problem from Step 3 can be augmented as:

$$\max_{f} \sum_{i=1}^{N}\sum_{j=1}^{M} f(i, j)\left[g(i, j) + \sum_{k=1}^{K} z(i, j, k)u_k\right]$$

$$\text{s.t.} \sum_{j=1}^{M} f(i, j) = 1 \forall\, i = 1, \ldots, N$$

$$\sum_{i=1}^{N} f(i, j) \geq \varphi_{Lo,j} \forall\, j = 1, \ldots, M$$

$$\sum_{i=1}^{N} f(i, j) \leq \varphi_{Hi,j} \forall\, j = 1, \ldots, M$$

$$\sum_{i=1}^{N}\sum_{j=1}^{M} f(i, j)z(i, j, k) \geq Met_{Lo,k} \forall\, k = 1, \ldots, K$$

$$\sum_{i=1}^{N}\sum_{j=1}^{M} f(i, j)z(i, j, k) \leq Met_{Hi,k} \forall\, k = 1, \ldots, K$$

$$f(i, j) \in \{0, 1\}$$

Some portions of the detailed description are presented in terms of algorithms and symbolic representations of operations on data bits within a computer memory. These algorithmic descriptions and representations can be used by those skilled in the computer and software related fields.

The algorithms and displays presented herein are not inherently related to any particular computer or other apparatus provided it is capable of executing a rules engine. Various general purpose systems may be used with programs in accordance with the teachings herein, or it may prove convenient to construct more specialized apparatus to perform the required method steps. The required structure for a variety of these systems will appear from the description below. In addition, the present invention is not described with reference to any particular programming language, and various embodiments may thus be implemented using a variety of programming languages.

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are intended to be embraced therein.

What is claimed is:

1. A method to assign patients to providers, the method comprising the steps of:

a. extracting patient records from at least one database, by one or more server computers in communication with the at least one database, for a plurality of patients and a plurality of providers to obtain data comprising patient attributes and provider metrics,
> wherein each patient is represented as a single feature vector and is associated with one or more provider-specific metric vectors in the data,
> wherein the respective feature vector comprises one or more patient attributes,
> wherein each provider-specific metric vector corresponds to a plurality of metrics including one or more of clinical outcomes, cost, patient satisfaction, length of stay, revenue, and margin;

b. training, by the one or more server computers, a plurality of metric-specific models corresponding to the plurality of providers based on the data,
> wherein each metric-specific model of the plurality of metric-specific models is configured to predict a respective metric corresponding to a respective provider of the plurality of providers,
> wherein the plurality of metric-specific models are trained simultaneously via multi-task learning;

c. receiving one or more patient attributes of a new patient;

d. inputting the one or more patient attributes of the new patient to the plurality of metric-specific models to obtain a plurality of metric-specific predictions corresponding to the plurality of providers;

e. determining an allocation of the new patient to a provider of the plurality of providers based on the plurality of metric-specific predictions with a goal of maximizing or minimizing, subject to operational constraints, one or more of the plurality of metrics, wherein the maximizing or minimizing includes reduction of clinical outcome based risk, improving finances and improving patient satisfaction; and f. assigning a case corresponding to the new patient to the provider based on the allocation.

2. The method as recited in claim 1, wherein the patient records are given increased importance based on at least one of: relevance and recentness of the patient records by upweighting or upsampling.

3. The method as recited in claim 1, wherein training the plurality of metric-specific models corresponding to the plurality of providers comprises one of:
> simultaneously, for all providers, utilizing a shared or joint machine learning approach; or
> independently, per provider, utilizing the machine learning approaches of transfer learning, semi-supervised learning, unsupervised learning, metric or subspace learning, and 1.5 class learning.

4. The method as recited in claim 1, wherein the data is selected from the group of historical, non-historical, and other data.

5. The method as recited in claim 4, further comprising using predicted probabilities of patient performance across providers for each performance metric in an objective function and constraints using models trained for each provider and for each metric.

6. The method as recited in claim 4, further comprising using mixed integer programming to assign patients to providers.

7. The method as recited in claim 4, further comprising using online optimization, sampling and simulation based on probabilistic priors, and greedy allocation to assign patients to providers.

8. The method as recited in claim 5, further comprising including a reward for exploration in the objective function.

9. The method as recited in claim 8, further comprising using active learning or multi-armed bandit information in the objective function.

10. A computer-based system to assign patients to providers, the computer-based system comprising:

a. at least one database of patient records of data comprising patient attributes and provider metrics for a plurality of patients and providers; and b. one or more processors of one or more server computers and one or more input/output devices, wherein the one or more server computers are in communication with the at least one database, the one or more processors performing the operations of:
> i. retrieving the data comprising the patient attributes and the provider metrics for the plurality of patients and providers through a query to the at least one database for historical records,
>> wherein each patient is represented as a single feature vector and is associated with one or more provider-specific metric vectors in the data,
>>> wherein the respective feature vector comprises one or more patient attributes, and
>>> wherein each provider-specific metric vector corresponds to a plurality of metrics including one or more of clinical outcomes, cost, patient satisfaction, length of stay, revenue, and margin;
>
> ii. training a plurality of metric-specific models corresponding to the plurality of providers based on the data, wherein each metric-specific model of the plurality of metric-specific models is configured to predict a respective metric corresponding to a respective provider,
>> wherein the plurality of metric-specific models are trained simultaneously via multi-task learning; and
>
> iii. receiving one or more patient attributes of a new patient;
>
> iv. inputting the one or more patient attributes of the new patient to the plurality of metric-specific models to obtain a plurality of metric-specific predictions corresponding to the plurality of providers;
>
> v. determining an allocation of the new patient to a provider based on the plurality of metric-specific predictions with a goal of maximizing or minimizing, subject to operational constraints, one or more of the plurality of metrics, wherein the maximizing or minimizing includes reducing clinical outcome based risk, improving finances, and improving patient satisfaction,
>
> wherein a case corresponding to the new patient is assigned to the provider based upon the allocation.

11. The computer-based system as recited in claim 10, wherein the patient records are given increased importance based on at least one of: relevance and recentness of the patient records by upweighting or upsampling.

12. The computer-based system as recited in claim 10, wherein training the plurality of metric-specific models corresponding to the plurality of providers comprises one of:
> simultaneously, for all providers, utilizing a shared or joint machine learning approach; or
> independently, per provider, utilizing the machine learning approaches of transfer learning, semi-supervised learning, unsupervised learning, metric or subspace learning, and 1.5 class learning.

13. The computer-based system as recited in claim 10, wherein new patients are assigned so as to maximize (or minimize), subject to operational constraints, an objective function corresponding to the assignment of patients to providers.

14. The computer-based system as recited in claim 12, wherein the training further comprises using predicted probabilities of patient performance across providers for each performance metric in an objective function and constraints using models trained for each provider and for each metric.

15. The computer-based system as recited in claim 10, wherein the assigning of a new patient to a provider is in response to using mixed integer programming to assign patients to providers.

16. The computer-based system as recited in claim 10, wherein the assigning of the new patient to the provider is in response to using online optimization, sampling and simulation based on probabilistic priors, and greedy allocation to assign patients to providers.

17. The computer-based system as recited in claim 14, wherein the training is in response to including a reward for exploration in the objective function.

18. The computer-based system as recited in claim 14, wherein the training uses active learning or multi-armed bandit information in the objective function.

19. The method of claim 1, wherein the plurality of metrics include at least two clinical outcomes.

20. The computer-based system as recited in claim 10, wherein the one or more input/output devices include at least two input/output devices.

\* \* \* \* \*